(12) United States Patent
Blacker

(10) Patent No.: US 10,085,805 B1
(45) Date of Patent: Oct. 2, 2018

(54) ROBOTICALLY SHAPING A GUIDE WIRE TIP

(71) Applicant: Corindus, Inc., Waltham, MA (US)

(72) Inventor: Steven J. Blacker, Framingham, MA (US)

(73) Assignee: CORINDUS, INC., Waltham, MA (US)

( * ) Notice: Subject to any disclaimer, the term of this patent is extended or adjusted under 35 U.S.C. 154(b) by 499 days.

(21) Appl. No.: 14/216,728

(22) Filed: Mar. 17, 2014

Related U.S. Application Data

(60) Provisional application No. 61/790,272, filed on Mar. 15, 2013.

(51) Int. Cl.
*A61B 5/00* (2006.01)
*A61F 2/02* (2006.01)
*A61B 19/00* (2006.01)
*A61M 25/09* (2006.01)

(52) U.S. Cl.
CPC ... *A61B 19/2203* (2013.01); *A61M 25/09041* (2013.01); *A61M 2025/09108* (2013.01)

(58) Field of Classification Search
CPC .................................................... A61B 5/00
USPC ......................................... 600/585; 604/528
See application file for complete search history.

(56) References Cited

U.S. PATENT DOCUMENTS

| | | | | |
|---|---|---|---|---|
| 5,957,941 A * | 9/1999 | Ream | .................. | A61B 8/12 600/443 |
| 6,096,004 A * | 8/2000 | Meglan | .................. | A61B 34/75 604/95.01 |
| 6,726,675 B1 * | 4/2004 | Beyar | ................ | A61M 25/0105 600/106 |
| 7,887,549 B2 | 2/2011 | Wenderow et al. | | |
| 8,257,302 B2 * | 9/2012 | Beyar | ...................... | A61B 5/00 600/106 |
| 8,600,477 B2 * | 12/2013 | Beyar | ...................... | A61B 6/12 128/899 |
| 8,694,157 B2 * | 4/2014 | Wenderow | ........... | A61B 5/7475 600/523 |
| 8,790,297 B2 * | 7/2014 | Bromander | ......... | G06F 19/3406 600/427 |
| 9,901,705 B2 | 2/2018 | Armour et al. | | |
| 2005/0277851 A1 * | 12/2005 | Whittaker | ......... | A61M 25/0158 600/585 |
| 2006/0253048 A1 * | 11/2006 | Jones | ............... | A61M 25/09041 600/585 |
| 2007/0106247 A1 * | 5/2007 | Burnett | ...................... | A61F 7/12 604/508 |
| 2007/0118079 A1 * | 5/2007 | Moberg | ..................... | A61F 2/95 604/164.07 |
| 2007/0276216 A1 * | 11/2007 | Beyar | ...................... | A61B 6/12 600/407 |
| 2008/0097298 A1 * | 4/2008 | Fisher | ............. | A61B 17/320758 604/103.04 |
| 2009/0247944 A1 * | 10/2009 | Kirschenman | ......... | A61B 90/10 604/95.04 |
| 2010/0130987 A1 * | 5/2010 | Wenderow | ......... | A61M 25/0113 606/130 |

* cited by examiner

*Primary Examiner* — May Abouelela
(74) *Attorney, Agent, or Firm* — Rathe Lindenbaum LLP

(57) ABSTRACT

A robotic system for driving a guide wire into a human patient includes a robotic tool to change shape the tip of the guide wire and a robotic control system providing signals to operate the guide wire shaping tool.

13 Claims, 3 Drawing Sheets

ROBOTICALLY SHAPING A GUIDE WIRE TIP

CROSS-REFERENCE TO RELATED PATENT APPLICATIONS

This application claims priority to U.S. Provisional Application No. 61/790,272 entitled ROBOTICALLY SHAPING A GUIDE WIRE TIP filed Mar. 15, 2013 and incorporated herein by reference in its entirety.

BACKGROUND

Guide wires are used to facilitate percutaneous procedures in which the guide wire is threaded into a human patient using X-ray guidance. The guide wires are manually threaded by a physician or other medical personnel but this requires that the operator be adjacent to the patient and so be in the immediate vicinity of the X-ray radiation providing the image used for guidance. Systems have been developed, such as that disclosed in U.S. Pat. No. 7,887,549 incorporated herein by reference, which allow the guide wires to be threaded into the patient robotically and thus allow the user or operator to be remote from the patient and the X-ray radiation. The tip of the guide wire may be manually shaped into an arcuate shape to assist in the navigation of the guide wire.

SUMMARY

In one embodiment a robotic system for driving a guide wire into a human patient includes a robotic tool to change shape the tip of the guide wire and a robotic control system providing signals to operate the guide wire shaping tool.

Another embodiment includes a process for changing the shape of a tip of a guide wire with a robotic drive including feeding a portion of a guide wire into a tip shaping mechanism. The process also includes robotically operating the tip shaping mechanism to cause the tip of the guide wire to be plastically deformed such that it is directed away from a longitudinal axis of the guide wire. The process further includes robotically feeding the guide wire with the shaped tip into a vessel in a human patient.

In another embodiment, a system for providing a robotically driven guide wire with a shaped tip to a guide catheter includes a tip shaping mechanism which causes the tip of the guide wire to be plastically deformed such that it is directed away from the axis of the guide wire. A robotic drive mechanism feeds the guide wire to the tip shaping mechanism.

DETAILED DESCRIPTION

Figure 1:
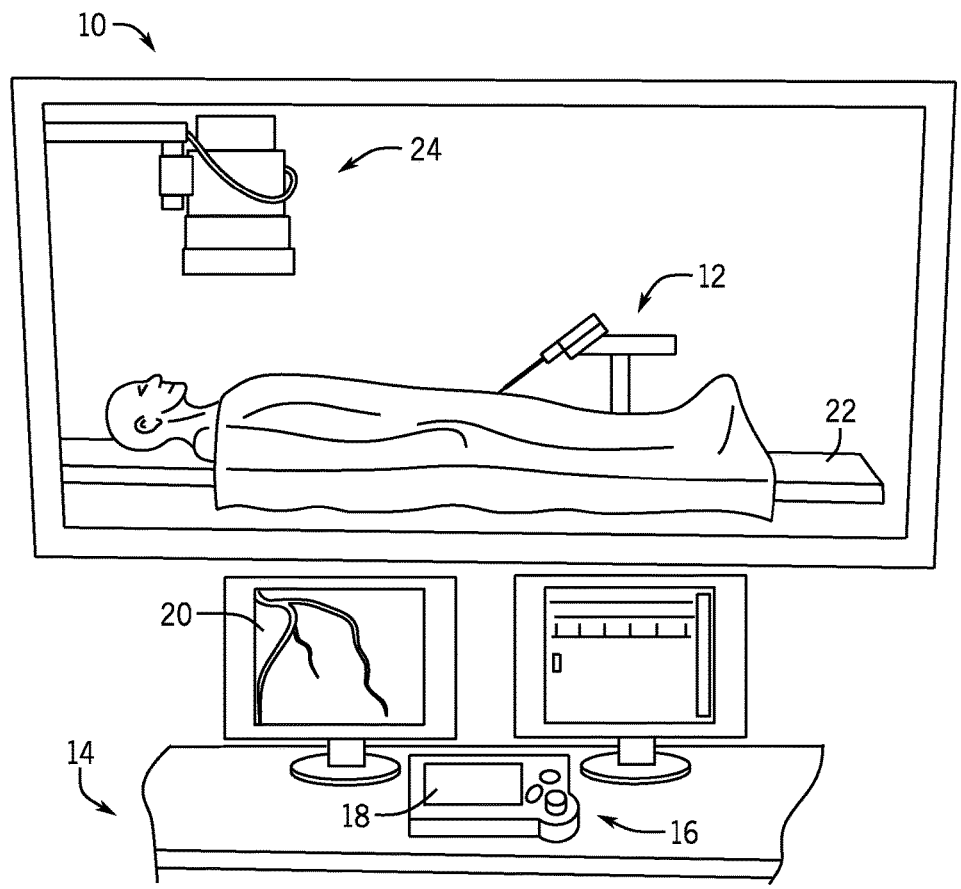
FIG. 1 is a schematic view of a robotic system for remotely moving a guide wire in a patient.

Referring to FIG. 1 a robotic system for manipulating an elongated medical device includes a bed side station 12 proximate a bed 22. A remote control station 14 includes a controller 16 having a user input 18 to control the bed side station 12. An x-ray source 24 is used in a Fluoroscopy system to provide an image on a display 20 in remote station 14. A robotic system such as that described in U.S. Pat. No. 7,887,549 may be used in conjunction with the wiper mechanism described herein.

Figure 2:
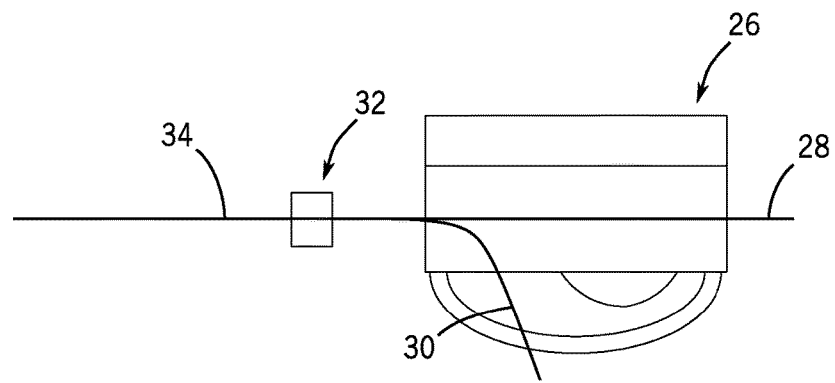
FIG. 2 to a schematic top plan view of a robotic drive and a wire shaping tool.

Referring to FIG. 2, in one embodiment a robotic shaping tool device 32 is positioned intermediate guide catheter 34 and the guide wire drive mechanism in cassette 26. It is also contemplated to position robotic shaping tool device 32 separate from cassette 26 or on a distal end portion of cassette 26. By positioning robotic shaping tool device 32 on the distal end or distal portion of cassette 26 it is possible to provide a shape to the guide wire tip without removing the guide wire from the drive mechanisms within cassette 26. In another embodiment, robotic shaping tool device 32 may be positioned on a proximal end of cassette 26. It is contemplated that a portion of the guide wire 28 may be positioned within the drive mechanism or mechanisms within cassette 26 and a sufficient length of the guide wire 28 may extend from the distal end of the cassette so that the tip may be shaped in a robotic shaping tool device 32 positioned above, below, to the right or left of cassette 26. In one embodiment a proposed tip shape could be tested using simulation software. A proposed tip shape could be run through a simulation and the results used to adjust how the shaping tools are instructed. In one embodiment, a working elongated medical device such as a balloon stent catheter 30 is driven longitudinally by a drive mechanism within cassette 26 and the robotic shaping tool device 32 is located between the drive mechanism for the working catheter and the guide catheter 32.

Figure 3:
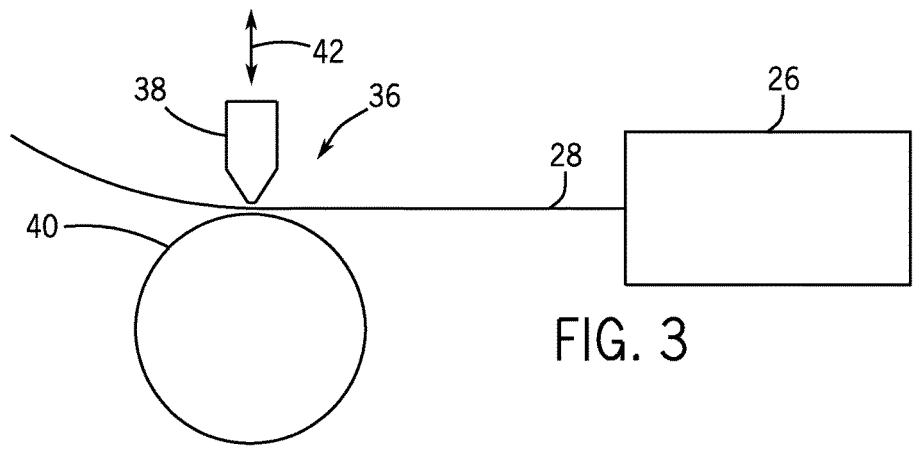
FIG. 3 is a schematic view of a first robotic wire shaping tool.

Referring to FIG. 3, robotic drive mechanism 26 feeds guide wire 28 to an anvil based tip shaping mechanism 36. Anvil based shaping mechanism 36 comprises an anvil 38 with angled faces and a cooperating wheel 40. An application force 42 can be applied to the anvil 38 at various angles to influence the shape imparted to the tip of the guide wire 28.

Figure 4:
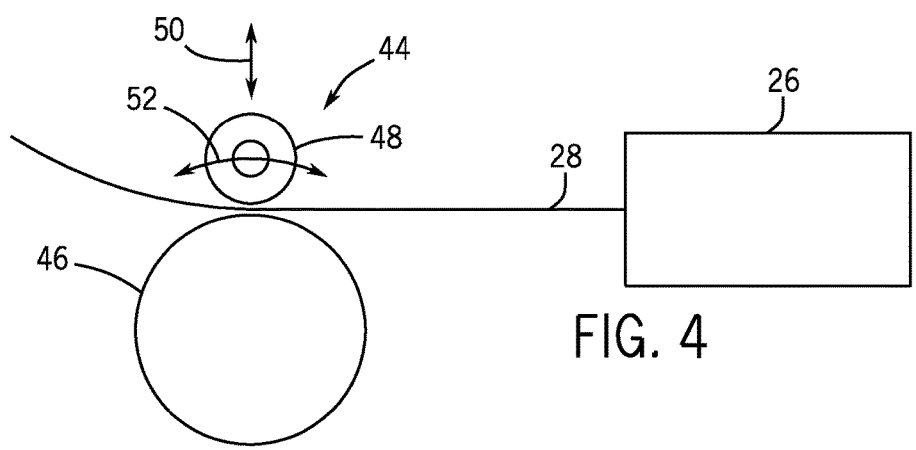
FIG. 4 is a schematic view of a second robotic wire shaping tool.

Referring to FIG. 4, robotic drive mechanism 26 feeds guide wire 28 to a roller based tip shaping mechanism 44. Roller based tip shaping mechanism 44 comprises a roller 48 and a cooperating wheel 46. Roller 48 has an adjustment path 52 which facilitates addressing guide wire 28 in such a way that the path of guide wire 28 is diverted from a straight line from drive 26 to mechanism 44. Force 50 causes roller 48 to press guide wire 28 against wheel 46.

Figure 5:
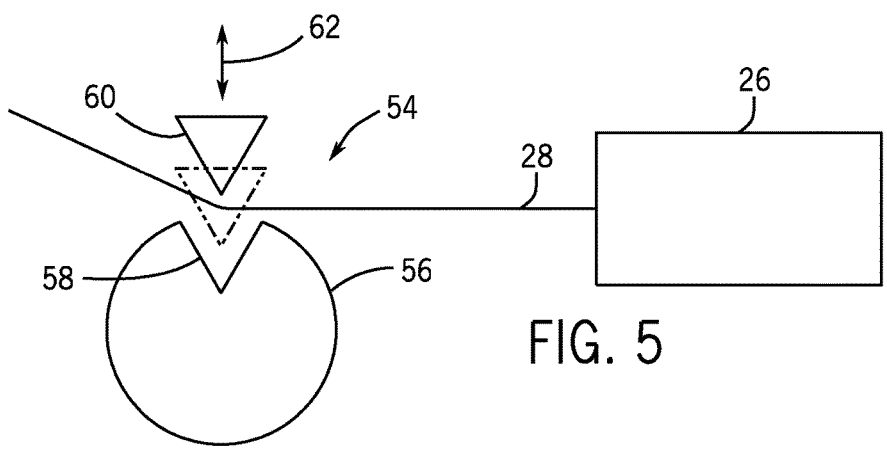
FIG. 5 is a schematic view of a third robotic wire shaping tool.

Referring to FIG. 5, robotic drive mechanism 26 feeds guide wire 28 to a fixed shaping tool based tip shaping mechanism 54. Fixed shaping tool based mechanism 54 comprises a finger 60 which is pressed into a shaped recesses 58 in a fixed shaping tool 56 by a force 62.

Figure 6:
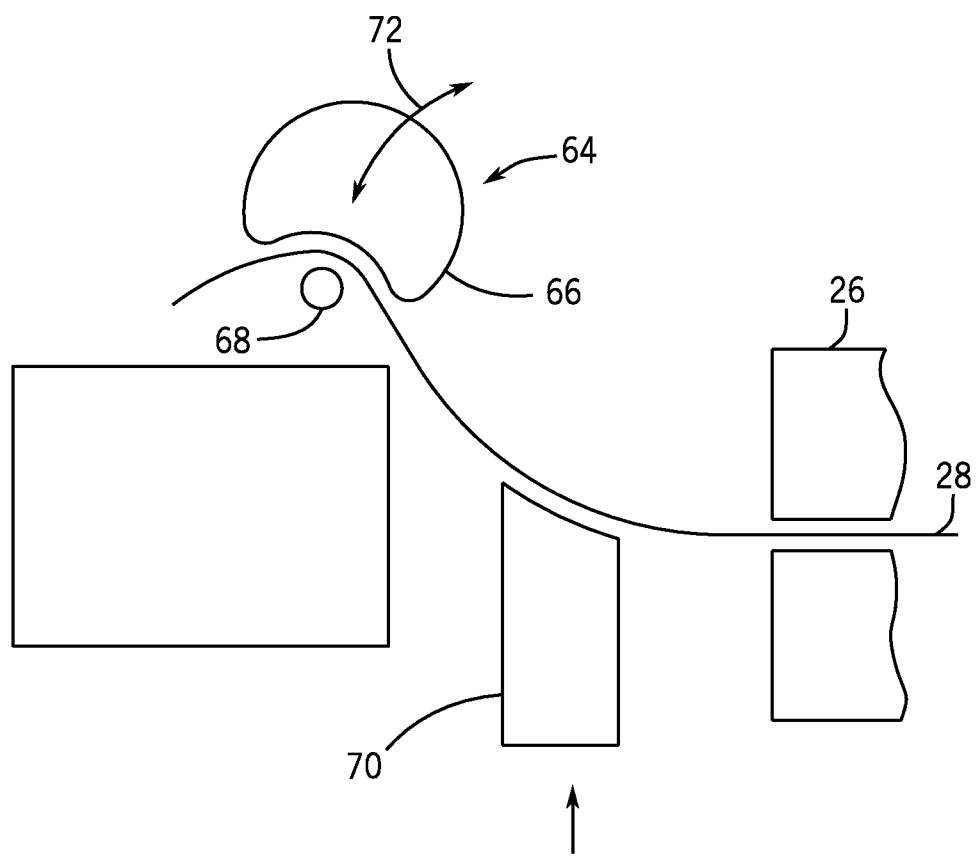
FIG. 6 is a schematic view of a fourth robotic wire shaping tool.

Referring to FIG. 6, robotic drive mechanism 26 feeds guide wire 28 to a variable shaping tool based tip shaping mechanism 64. Variable shaping tool based shaping mechanism 64 comprises a variable shaping tool 66 and a cooperating cylindrical finger 68. Variable shaping tool 66 has a variable surface and force 72 determines what portion of that face interacts with guide wire 28 and cylindrical finger 68. The portions of shaping tool 66 that contact guide wire 28 may be elastomeric. A diverter 70 directs guide wire 28 along a first path from robotic drive 26 to mechanism 66.

In one embodiment the tip of the guide wire is forced against a post or anvil with an appropriately shaped tool to angle the tip away from the axis of the guide wire. The action is similar to the action of drawing a decorative packaging ribbon over a scissors to impart a curl. In one embodiment the anvil and tool are positioned between the end of the robotic system which delivers the guide wire and the human patient and in another embodiment it is placed earlier in the delivery path. In the former case it may be necessary to withdraw the guide wire, shape its tip and then retract the guide wire while in the latter case it may be possible to shape the tip as the guide wire is being feed through the robotic system. Two approaches to shaping tools positioned in accordance with the former approach are shown in the attached drawing.

In one embodiment the controls for the tools such as the anvil or post and shaping tool may include suggested shaping routines. In one embodiment the system may contain software that examines an X-ray image of the anticipated path of the guide wire and then proposes a particular shaping routine.

In one embodiment the system may provide an image of the shaped tip to the user. This would allow the user to operate the tools to better conform the tip to the desired shape in cases in which the initial routine failed to do. Thus the image could act as a quality control and eliminate the need to leave the control console and physically inspect the shaped tip.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. Any of the features, elements, or components of any of the exemplary embodiments discussed above may be used alone or in combination with any of the features, elements, or components of any of the other embodiments discussed above. It is to be understood that the forms of the invention shown and described herein are to be taken as presently preferred embodiments. Elements and materials may be substituted for those illustrated and described herein, parts and processes may be reversed, and certain features of the invention may be utilized independently, all as would be apparent to one skilled in the art having the benefit of this description of the invention. Changes may be made in the elements described herein without departing form the spirit and scope of the invention as described in the following claims.

What is claimed is:

1. A process for deforming a shape of a tip of a guide wire with a robotic system having a drive for a percutaneous procedure and including a control system providing control signals to operate a tip shaping mechanism comprising:

feeding a portion of the guide wire having the tip into the tip shaping mechanism having a first member and a second cooperating member;

operating the tip shaping mechanism to move the first member relative to the second cooperating member with the tip of the guide wire therebetween to cause the tip of the guide wire to be deformed such that the tip is directed away from a longitudinal axis of the guide wire; and wherein the guide wire is fed into the tip shaping mechanism with a drive mechanism and a diverter to divert the guide wire from a straight line from the drive mechanism to the tip shaping mechanism;

feeding the guide wire with the deformed tip into a guide catheter.

2. The process of claim 1 wherein the guide wire is fed to the tip shaping mechanism following a first path, then withdrawing the guide wire with the deformed tip into a feeding mechanism and then feeding the guide wire with the deformed tip along a second path into the guide catheter.

3. The process of claim 1 wherein the tip shaping mechanism lies along a path that leads into the guide catheter.

4. The process of claim 1 including providing a simulation of the deformed tip along path—the guide wire is to follow.

5. The process of claim 1 wherein the operation of the tip shaping mechanism involves moving the guide wire along the longitudinal axis of the guide wire.

6. The process of claim 5 wherein a speed at which the guide wire is moved past the tip shaping mechanism is used to affect the tip shape.

7. The process of claim 5 wherein an angle between the guide wire of the tip shaping mechanism is used to affect the tip shape.

8. The process of claim 1 wherein a portion of the tip shaping mechanism includes elastomeric material.

9. The process of claim 1, wherein feeding the guide wire with the deformed tip into the guide catheter includes using the robotic system to robotically feed the guide wire.

10. A system for providing a guide wire with a deformed tip to a guide catheter for a percutaneous procedure with a robotic system with a control system providing control signals to operate a tip shaping mechanism, comprising:

a guide catheter;

the tip shaping mechanism causes the tip of the guide wire to be plastically deformed such that the tip is directed away from a longitudinal axis of the guide wire; and a drive mechanism that feeds the guide wire to the tip shaping mechanism and feeds the guide wire with the deformed tip into a guide catheter;

the tip shaping mechanism including a diverter configured to divert the guide wire from a straight line from the drive mechanism to the tip shaping mechanism;

wherein the tip shaping mechanism is positioned intermediate the drive mechanism and the guide catheter.

11. The system of claim 10 wherein the tip shaping mechanism comprises a finger that presses the guide wire into a shaping tool.

12. The system of claim 11 wherein a portion of the shaping tool that interacts with the guide wire is elastomeric.

13. The system of claim 10, wherein the system further includes an imaging mechanism that creates an image of the deformed tip and provides the image to an operator of the system.

* * * * *